Figure 1:
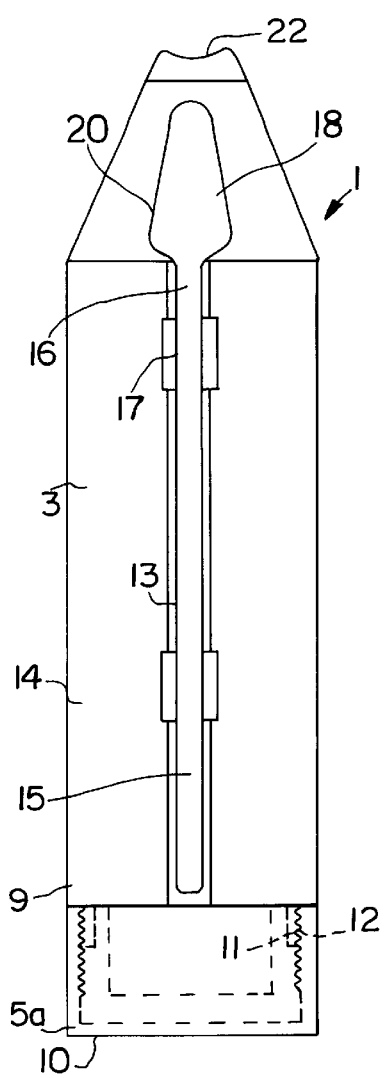

United States Patent

Hecker et al.

[11] Patent Number: 5,922,292
[45] Date of Patent: Jul. 13, 1999

[54] CARE STATION FOR TOOTHBRUSHES

[76] Inventors: Frithjof Hecker, Rubkerstrasse 6c, D-21614 Buxtehude; Norman Duczek, Dibberser Muhlenweg 17, D-21244 Buccholz, both of Germany

[21] Appl. No.: 08/849,434
[22] PCT Filed: Nov. 24, 1995
[86] PCT No.: PCT/DE95/01680
  § 371 Date: May 23, 1997
  § 102(e) Date: May 23, 1997
[87] PCT Pub. No.: WO96/16750
  PCT Pub. Date: Jun. 6, 1996

[30] Foreign Application Priority Data

Nov. 26, 1994 [DE] Germany ............... 44 42 183

[51] Int. Cl.⁶ ............................................. A61L 2/18
[52] U.S. Cl. ................ 422/300; 422/292; 206/209.1; 206/362.2
[58] Field of Search ................. 422/300, 301, 422/292; 206/209.1, 362.2

[56] References Cited

U.S. PATENT DOCUMENTS

| | | |
|---|---|---|
| 1,278,789 | 9/1918 | Thompson ........................ 422/300 |
| 1,584,261 | 5/1926 | Vuolo ............................... 422/300 |
| 4,997,629 | 3/1991 | Marchand et al. ................ 422/300 |
| 5,145,095 | 9/1992 | Loudon ............................ 222/181 |
| 5,405,587 | 4/1995 | Fernandez et al. ............... 422/292 |

FOREIGN PATENT DOCUMENTS

| | | |
|---|---|---|
| 2802933 | 7/1979 | Germany . |
| 3937023 | 5/1991 | Germany . |
| 2232581 | 12/1990 | United Kingdom . |

*Primary Examiner*—Terrence R. Till
*Assistant Examiner*—Fariborz Moazzam
*Attorney, Agent, or Firm*—Bierman, Muserlian and Lucas

[57] ABSTRACT

In a toothbrush cleaning station, the bristles of a toothbrush are brought into contact with a disinfectant. The toothbrush cleaning station has a spraying device for the disinfectant to be sprayed on the bristles and a support for the bristles of the toothbrush in the disinfectant spraying area. A holder holds the toothbrush and at the same time forms a holder for the can-shaped spraying device. The holder for the spraying device retains it in a position in which the bristles of the toothbrush remain in the disinfectant spraying area.

14 Claims, 6 Drawing Sheets

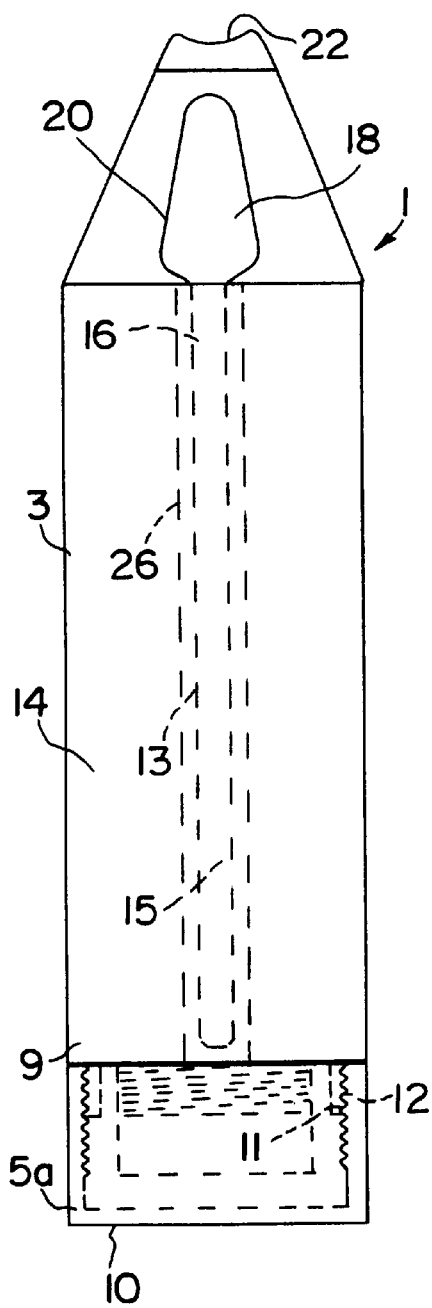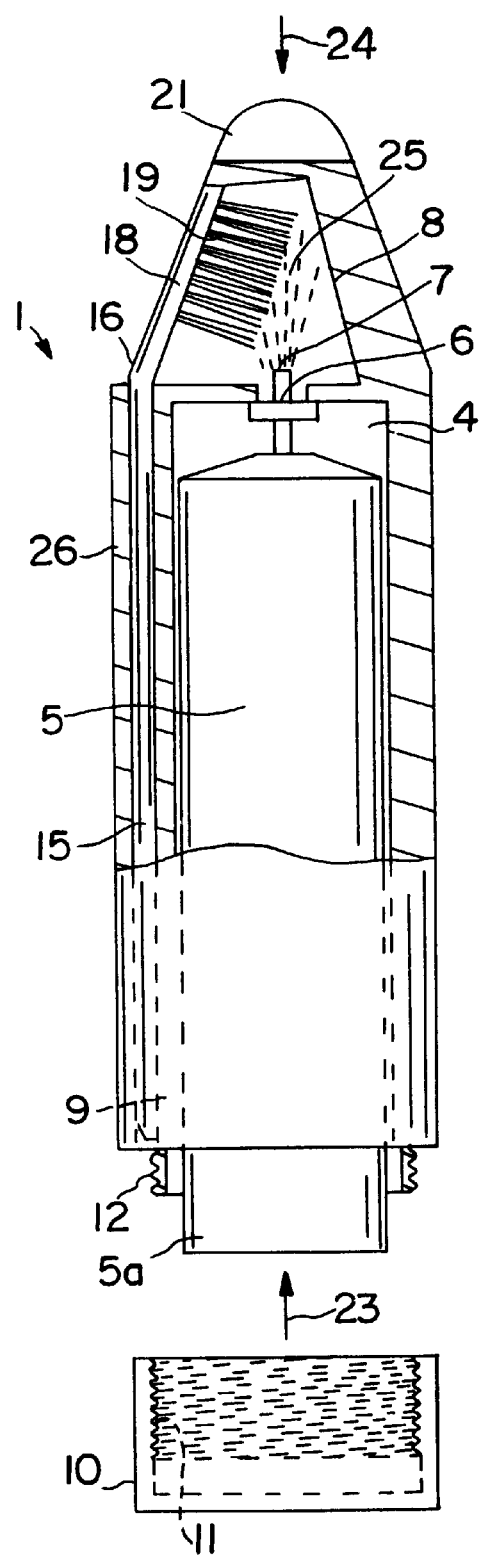
FIG. 3
FIG. 4

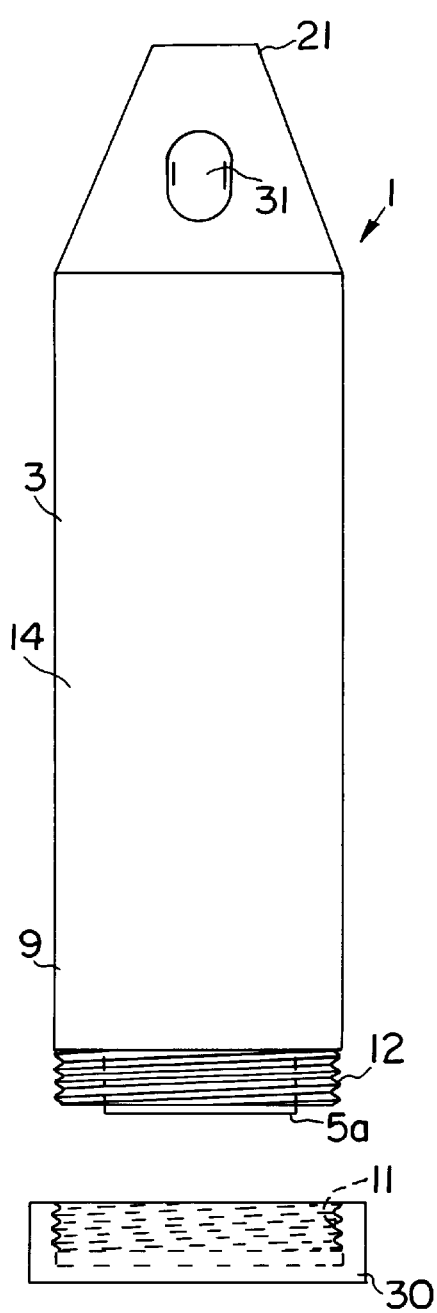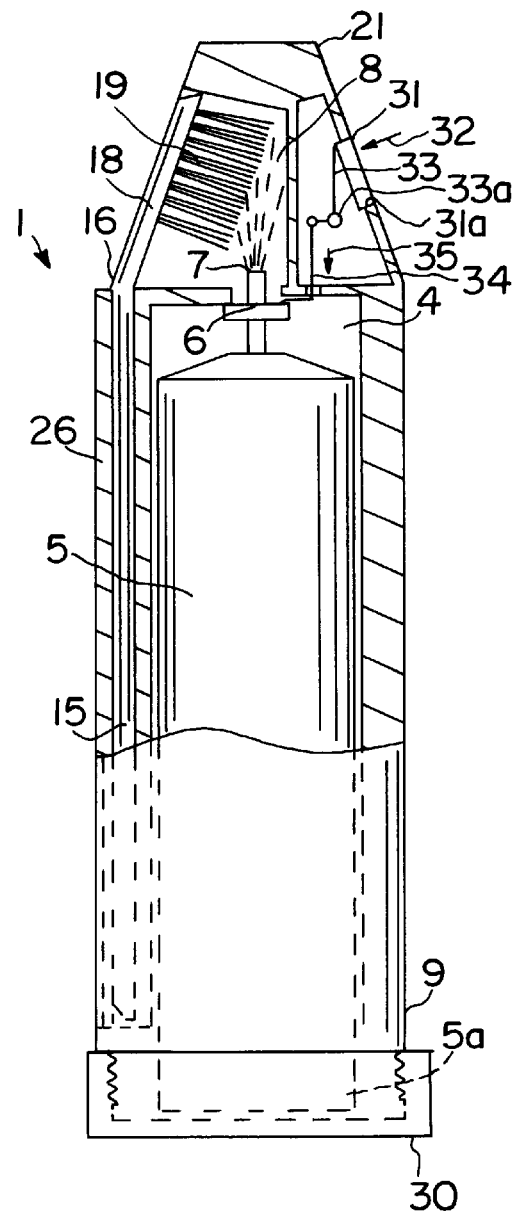
FIG. 5
FIG. 6

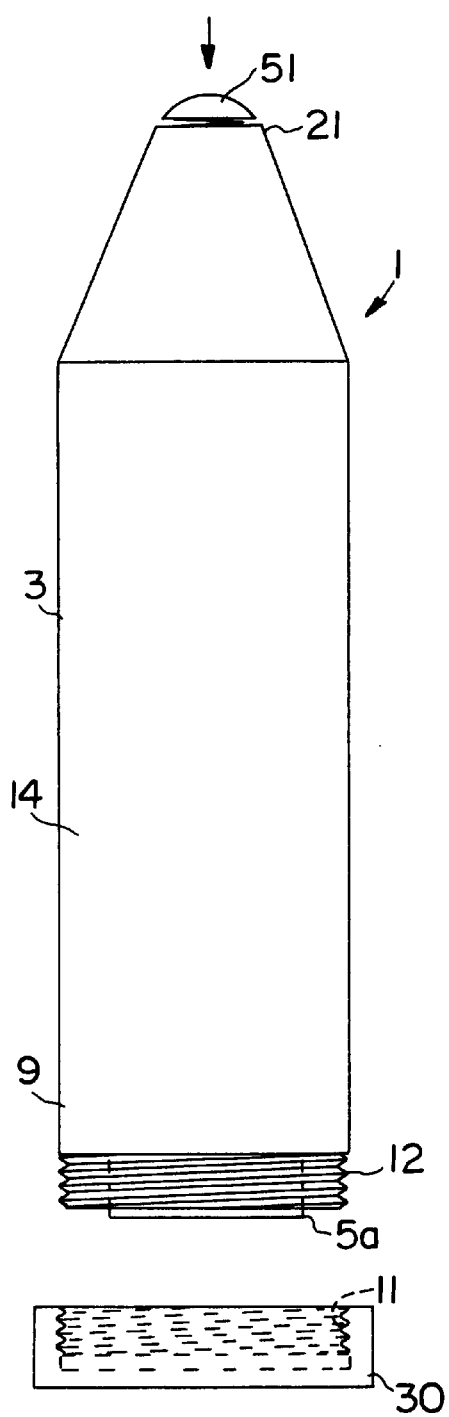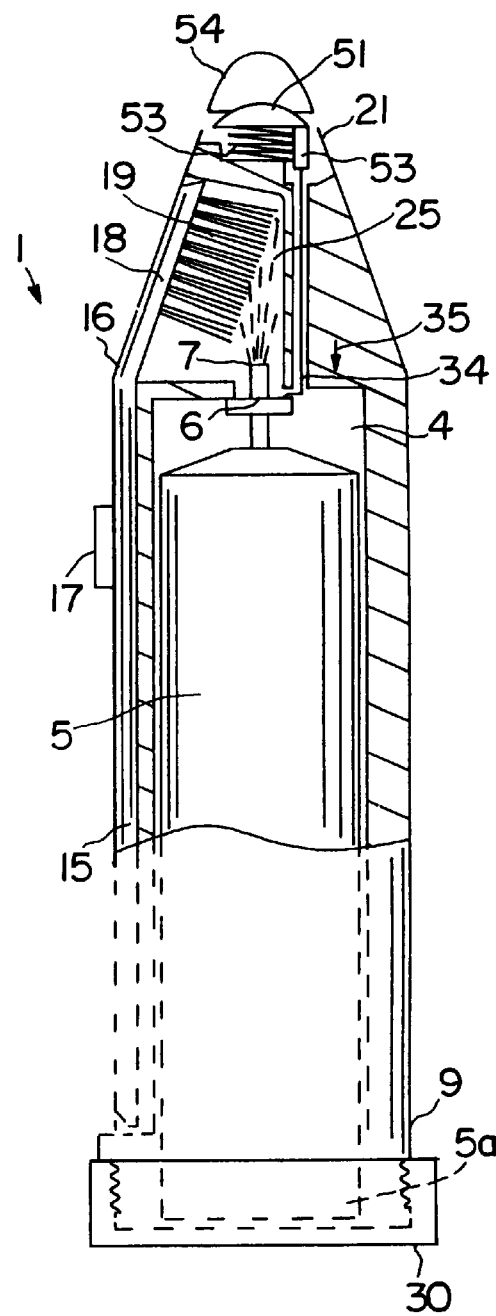
FIG. 8
FIG. 9

CARE STATION FOR TOOTHBRUSHES

The invention relates to a care station for toothbrushes, in which the bristles of a toothbrush are contacted with a disinfectant medium and which has both a spraying device for the medium to be sprayed on the bristles and a bedding, at which the bristles of the toothbrush are situated within the spray region of the medium.

Nowadays a lot of attention is paid to the oral and dental care in order to prevent dental diseases. In this connection a number of cleaning agents and disinfectants are used, the activity spectra of which are all directed to the surfaces of the teeth. To disinfect toothbrushes it is known from DE 28 02 933 Al to dip the bristles of a toothbrush in a cup after using it, in which cup a disinfectant fluid is contained. It is also possible to arrange several cups side by side. In this method of disinfecting much more disinfectant fluid is required than in principle is necessary for disinfection.

In addition, from DE 39 37 023 Al a device for thermally disinfecting various products, such as dental appliance, toothbrushes, baby utensils or medical instruments is known. A closed container with a receiving basket for the products is used for this, which has a water heating system and a pumping device. The water heated by means of the heating is circulated by the pump and sprayed on the products contained the receiving basket for disinfection.

For an individual cleaning of toothbrushes that device is too expensive. Moreover it requires a disproportionately large amount of energy and medium in the case of an individual cleaning due to the relatively large amount of water to be circulated.

It is the object of the invention to make the disinfection more efficient and to render the device used for disinfection also transportable for a journey.

The set task is solved according to the invention by a support, which forms a holding device for the toothbrush and at the same time a holding device for the can-shaped spraying device, wherein it can be held in place by means of the holding device for the can-shaped spraying device such that the bristles of the toothbrush are situated within the spray region of the medium passing out of it.

By means of the spraying device the bristles of a toothbrush can be disinfected and cleaned, for which only a push of a spray jet is required. Thus only little disinfectant, care or cleaning medium is required for a complete disinfection or cleaning. The uniform holding device for a toothbrush designed as a support and a can-shaped spraying device simplify the toothbrush care station.

According to a further embodiment of the invention it is provided that the extremely limited spray region only impinges on the bristles of a toothbrush in an exactly oriented manner. This allows a very selective disinfection.

According to a further embodiment of the invention it is provided that the holding device for the spraying device forms a receiving space for the latter. This way the spraying device is fully included in the station.

According to a modified embodiment of the invention it is provided that the spraying device can be clamped to the support by means of the holding device. Here clamping may take place in such a manner that the spraying device can be clamped to the support by means of clamping arms springing towards each other. This manner of separable attachment is simple and particularly saves material.

According to a further embodiment of the invention it is provided that the toothbrush can be clamped to the wall of the support. Another way of fixing is that the toothbrush can be inserted into a receiving shaft at the wall of the support.

In again another way of arrangement it is provided that the toothbrush can be clamped to the inner side of a closing cap.

According to a further embodiment of the invention an advantageous embodiment of placing the toothbrush consists in the fact that it can be placed in a depression of a toothbrush case provided on the support, which case is closable with a hinged closing cap.

According to a further embodiment of the invention it is provided that the support has a bristle chamber, into which a push of a spray mist of the spraying device can be introduced and in which the bristles of the toothbrush are situated when the toothbrush is positioned in the spraying position.

Spraying thus takes place in a closed limited space, in which the bristles may remain until the toothbrush is used again.

According to a further embodiment of the invention it is provided that the toothbrush and the spraying device are arranged with their heads pointed downwards.

According to a further embodiment of the invention it is provided that by pushing in the bottom region of the spraying device its valve can be openend and thus the push of a spray mist can be released from the spraying device. By pressing the spraying device into the housing the disinfection is hence initiated.

According to a further embodiment of the invention it is provided that a covering cap can be placed over the bottom region of the spraying device, which secures the bottom region against unintentional pushing in. This is of particular importance if the care station is taken along on a journey.

According to a further embodiment of the invention it is provided that the covering cap is equipped with a release mechanism pressing the spray can into the support. A release mechanism in the covering cap reduces the risk of an unintentional actuation.

According to a further embodiment of the invention it is provided that the release mechanism consists of a turning knob, which upon turning is extended in the direction of the bottom of the spraying device such that it pushes the spraying vice into the support and with this actuates the push of a spray mist.

According to a further embodiment of the invention it is provided that the covering cap can be attached to the support by means of a bayonet joint.

According to a further embodiment of the invention it is provided that a finger depression for a finger is provided at the head of the support, which finger can be pressed against the finger depression to actuate the push of a spray mist. Thereby the operation is made easier.

In another embodiment of the invention it is provided that a release member is provided on the support, which, actuating a push of a spray mist, is able to act on the valve of the spraying device by an adjusting device. Such an embodiment is easier to operate, because it is not necessary to push parts of the device against each other.

Figure 2:
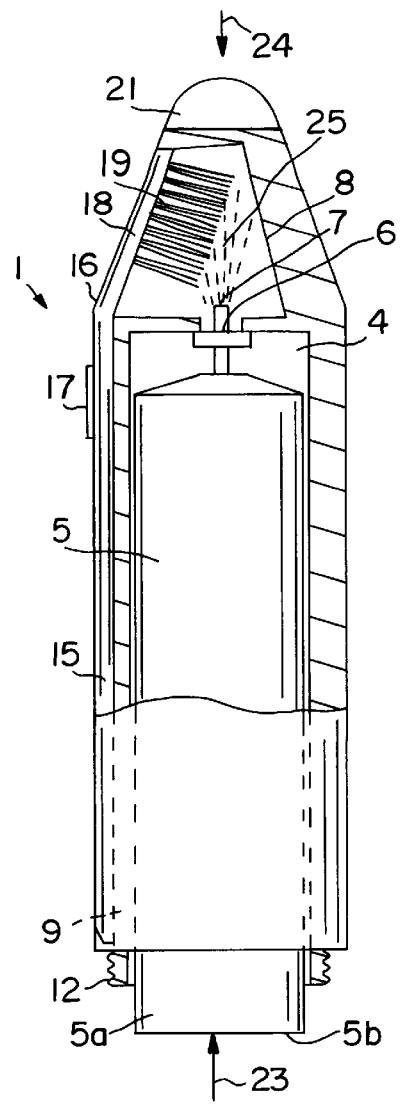
Figure 7:
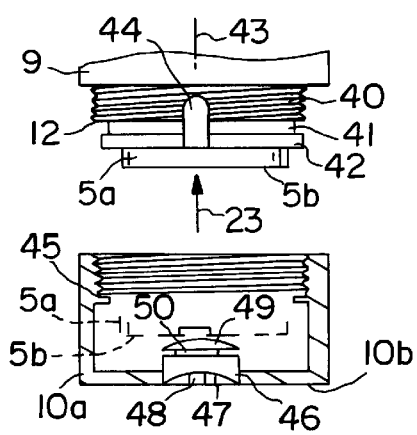
Figure 10:
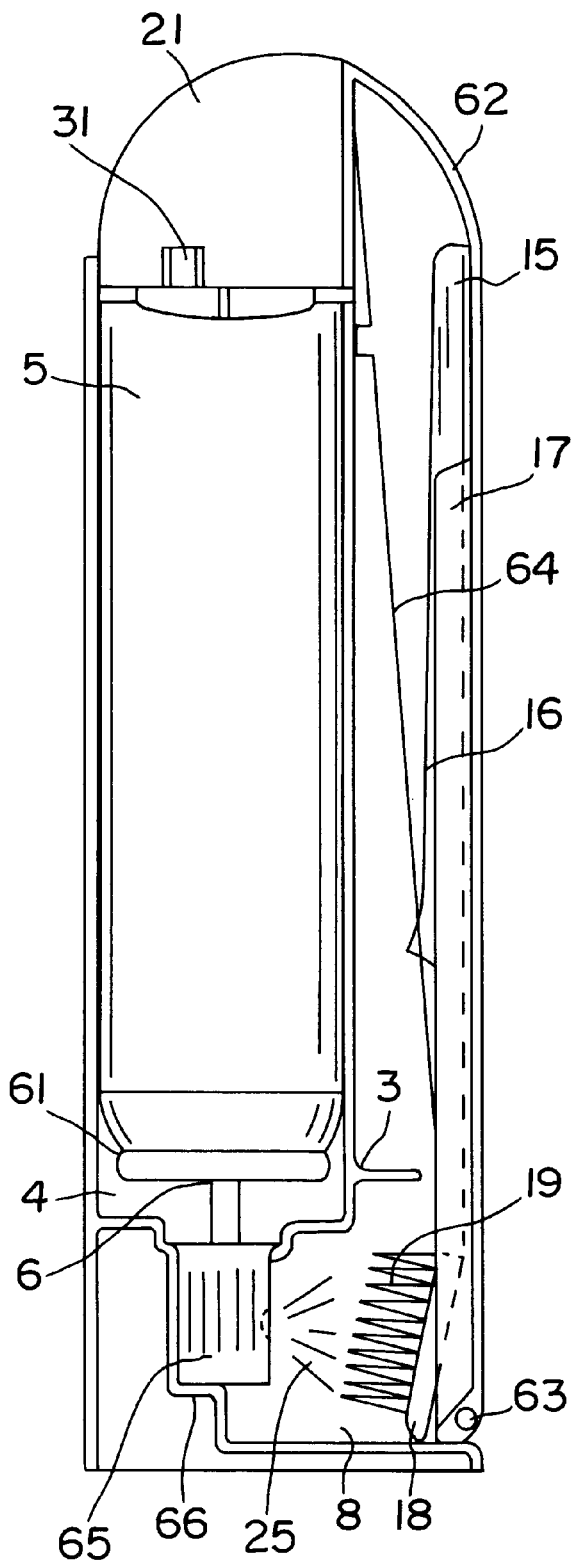
Figure 11:
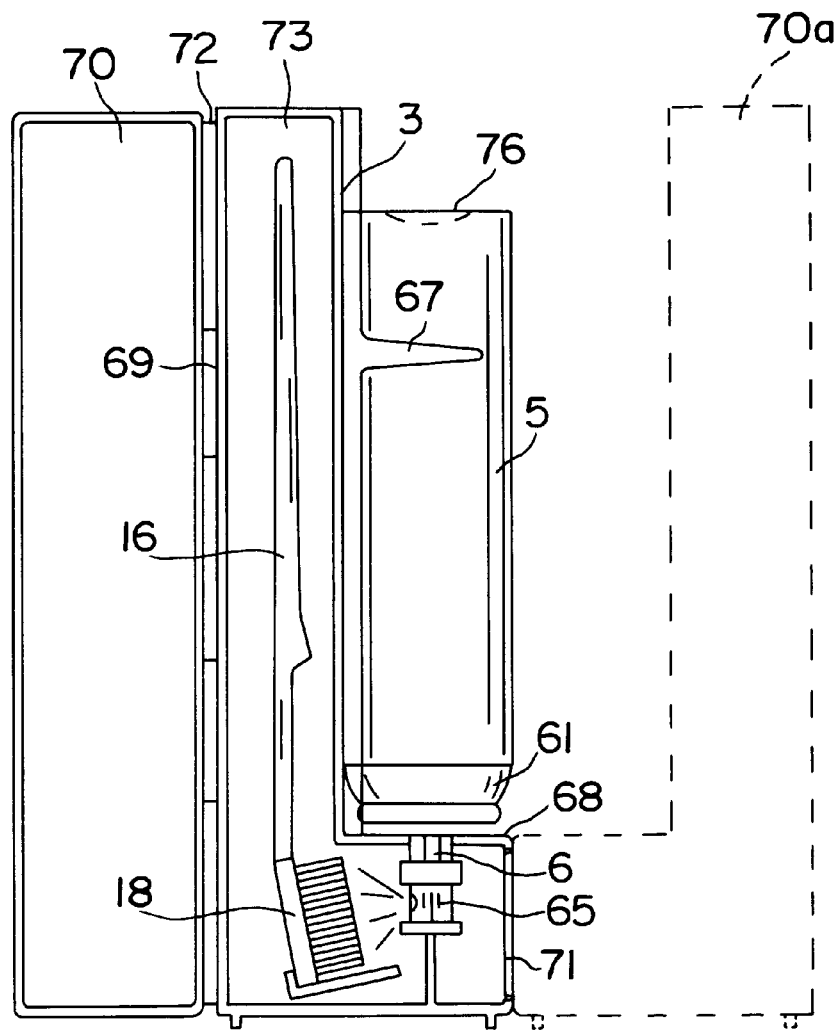

The invention is explained in greater detail by means of the drawing, in which:

FIG. 1 shows a view through a toothbrush care station according to the invention having a spraying device with which the bristles of a toothbrush can be sprayed, seen from the side of the housing of the device, to which the toothbrush is clamped, FIG. 2 shows a partial section through the toothbrush care station, FIG. 3 shows another embodiment of the toothbrush care station in side view, in which the toothbrush is placed in its care position in a sort of bag, FIG. 4 shows a partial section through the toothbrush care station according to FIG. 3, FIG. 5 shows a special embodiment of a covering cap equipped with a bayonet joint, FIG. 6 shows a further embodiment of the tooth care station with the toothbrush and the spraying device turned upside down, the toothbrush being arranged in a closing cap, FIG. 7 shows a further embodiment, in which the spraying device is only connected by clamps at the side and the toothbrush is situated in a case forming part of the support of the tooth station, FIG. 8 shows a top view of the embodiment according to FIG. 7.

In FIG. 1 a toothbrush care station 1 is shown. This toothbrush care station 1 consists of a support 3, which separably fastens both a spraying device 5 and a toothbrush 16. The holding device of a spraying device 5 designed in the shape of a can consists of a cavity 4, into which a spraying device 5 can be inserted. This spraying device 5 consists of a spray can, which can function with or without compressed gas. For that purpose this spray can 5 is equipped with a valve 6, the spray opening 7 of which extends into a bristle chamber 8 of the support 3.

At its end 9 lying at a distance from the bristle chamber 8 the support 3 is open, so that the spray can 5 can project from that end 9 with its bottom part 5a. In order to prevent an unintentional actuation of the spray can, a travelling blocking cap 10 is placed over the bottom part 5a during transport, as is shown in FIG. 1. To fix the cap that travelling blocking cap 10 has a female thread 11, which can be screwed on to a male screw thread 12 projecting from the end 9 of the support 3.

The handle 15 of a toothbrush 16 can be placed in a groove 13 on the wall 14 of the support 3. The toothbrush 16 is clamped in the groove 13 by means of clamping lugs 17. The head portion 18 of the toothbrush 16, or only the bristles 19 provided on it project into the bristle chamber 8 through an opening 20. The bristle chamber 8 is thus closed on all sides except for the opening 20 for the bristles 19 and the valve 6. A finger depression 22 is situated on the head 21 of the support 3 to facilitate the actuation.

In FIG. 2 two arrows 23 and 24 directed against each other are shown, by means of which the method of actuating the toothbrush care station is suggested. If the bottom part 5a of the spray can 5 is put on a rest or held in place in another way, which is indicated by the arrow 23, and it is pushed on the head 21 or the finger depression 22, respectively (arrow 24), the valve 6 is opened. With this a spray mist 25 passes out of the valve 6, flows into the bristle chamber 8 and moistens the bristles 19. The mist of the medium sprayed on the bristles can be germicidal, hence an antiseptic, and/or a deodorant preferably containing aromatic odorous substances. The medium can be released by means of compressed gas or by pumping action.

FIG. 3 and 4 show another embodiment of the housing. Here the handle 15 of the toothbrush is inserted into a receiving shaft 26 of the support 3. Like that the toothbrush 16 is well secured against unintentional falling off, in particular on a journey.

FIG. 5 shows another embodiment of the covering cap 10 according to FIG. 1 to 4 in combination with a modification of the slide-in end 9 of the housing 3. A groove 41 and an end flange 42 are adjacent to a few windings 12 of the threaded portion 40. Furthermore diametrically opposite sliding grooves 44 running in longitudinal direction 43 are provided in the threaded portion 40. The covering cap 10a belonging to it again has the thread 11 and in addition noses 45, which diametrically point towards each other.

In the bottom 10b of the covering cap 10a a turning knob 46 is provided, which has an arch 47 and a crosspiece as a handle 48. By turning the turning knob 46, the upper side 49 of a safety knob 50 can be pushed against the bottom area 5b and with that the valve of the spray can 5 can be opened.

The assembly of the covering cap 10a serves to secure the spray can 5 in the housing 3. Completely screwed on, the covering cap 10a fits tightly on the threaded portion 40 and protects against an unintentional actuation of the spray can 5. By turning the covering cap 10a the noses 45 get into the longitudinal slots 44. Like that the covering cap 10a can be taken off. If the turning knob 46 is turned with the covering cap 10a screwed on and the safety cap 50 is thereby lifted, a push of a spray mist 25 is actuated.

FIG. 6 shows a modification of the tooth care station, in which the head portion 18 of the toothbrush 16 and the head 61 of the spray can 6 are situated down at the bottom. The spray can is seated in the receiving cavity 4, and the toothbrush 16 is positioned in a closing cap 62, which is swivelling about a hinge 63 provided on the support 3. Clamping jaws 17 separably hold the toothbrush 16 in place. An opening spring 64 is provided which makes opening of the closing cap 62 easier. The spray head 65 of the valve 6 is seated in a seat 66 at the bristle chamber 8. Like that the spray mist 25 can be selectively passed on the bristles 19 of the toothbrush 16.

The spray mist 25 is actuated when the spray can 5 is pushed downwards by depressing the key 31 on the head 21 of the support.

Figure 12:
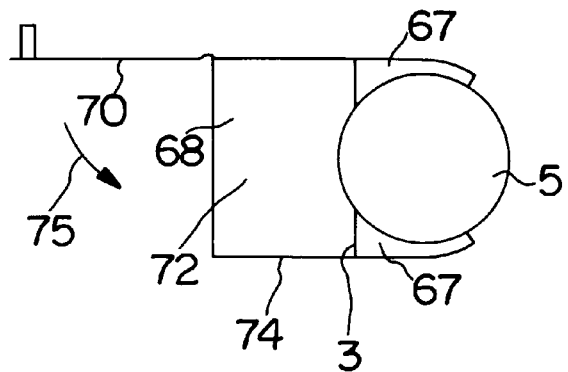

FIG. 7 shows a modification of the tooth care station with the toothbrush 16 and the spray can 5 turned upside down. In this embodiment the spray can 5 is situated freely at the support 3. The support 3 is provided with clamped arms 67 which embrace the spray can 5. The mode of action of the clamped arms 67 can be seen particularly well from FIG. 12. The valve 6 of the spray can 5 rests on a wall 68 of the bristle chamber 8 and extends into the bristle chamber 8 through that wall 68. In the bristle chamber 8, the spray head 65 is put on the valve 6. A case chamber 73 of a toothbrush case 72 is an integral part of the support 3. The toothbrush 16 can be placed in the case chamber 73 such that its bristles 19 come into the spray region opposite the spray head 65. In FIG. 7 the front wall of the case chamber 73 is removed for the sake of a better view. From FIG. 12 that wall 74 can be seen. The case chamber 73 is connected with a case lid 70 by hinge joints 69. When this case lid 70 is shut in the direction of an arrow 75 according to FIG. 8, the case is closed.

The broken line indicates a modification of the lid 70a. In this modification the case chamber 73 and the bristle chamber 8 are open to the front. The variant of the lid 70a is attached to a wall 71 of the bristle chamber 8 by means of a hinge joint. When the lid variant 70a is shut, both the case chamber 73 and the bristle chamber 8 are closed.

The spray can 5 is actuated by pressing its bottom 76.

We claim:

1. A care station for at least one toothbrush comprising:
a spraying device in a carrier, said spraying device releasing a disinfectant medium to contact bristles of at least one toothbrush positioned in a bristle chamber, said spraying device further having a bottom floor region,
a common support in the carrier with holding devices for both the spraying device and for the toothbrush, said common support further fastening both the toothbrush and the spraying device in their respective holding devices separately from but in spraying relation to each other, a valve with a spray head projecting into the bristle chamber, said valve laying against a seat of the common support so that the valve is opened by pushing the bottom floor region of the spraying device into the seat of the common support whereby the valve is opened whereby the medium is released from the spraying device onto the toothbrush bristles.

2. The care station as claimed in claim 1, wherein the toothbrush (16) and the spraying device (5) are arranged with their heads pointed downwards.

3. The care station as claimed in claim 1, wherein the support (3) has a bristle chamber (8), into which a push of a spray mist (25) of the spraying device (5) can be introduced and in which the bristles (19) of the toothbrush are situated when the toothbrush (16) is positioned in the spraying position, only one toothbrush (16) being used.

4. The care station as claimed in claim 1, wherein the spraying device (5) can be clamped to the support (3) by means of the holding device (67).

5. The care station as claimed in claim 4, wherein the spraying device (5) can be clamped to the support (3) by means of clamping arms (67) springing towards each other.

6. The care station as claimed in claim 4, wherein the toothbrush (16) can be clamped to the wall (14) of the support (3).

7. The care station as claimed in claim 1, wherein the toothbrush (16) can be inserted into a receiving shaft at the wall (14) of the support (3).

8. The care station as claimed in claim 1, wherein the toothbrush (16) can be clamped to the inner side of a closing cap (62).

9. The care station as claimed in claim 1, wherein the toothbrush (16) can be placed in a chamber (73) of a toothbrush case (72) provided on the support (3), which case is closable with a hinged cap (70, 70a).

10. The care station as claimed in claim 1, wherein a covering cap (10, 10a) can be placed over the bottom region (5a) of the spraying device (5), which secures the bottom region (5a) against unintentional pushing in.

11. The care station as claimed in claim 10, wherein the covering cap (10a) is equipped with a release mechanism (46) pressing the spraying device (5) into the support(3).

12. The care station as claimed in claim 11, wherein the release mechanism (46) consists of a turning knob, which upon turning is extended in the direction of the bottom (5b) of the spraying device (5) such that it pushes the spraying device (5) into the support (3) and with this actuates the push of a spray mist (25).

13. The care station as claimed in claim 11, wherein the covering cap (10a) can be attached to the support (3) by means of a bayonet joint (41, 44, 45).

14. The care station as claimed in claim 1, wherein a medium disinfecting at normal temperatures serves as a spray medium.

* * * * *